United States Patent [19]

Fitzpatrick et al.

[11] Patent Number: 5,451,504
[45] Date of Patent: Sep. 19, 1995

[54] METHOD AND DEVICE FOR DETECTING THE PRESENCE OF ANALYTE IN A SAMPLE

[75] Inventors: Judith Fitzpatrick, Tenafly, N.J.; Regina B. Lenda, Wesley Hills, N.Y.

[73] Assignee: Serex, Inc., Maywood, N.J.

[21] Appl. No.: 737,091

[22] Filed: Jul. 29, 1991

[51] Int. Cl.[6] .................. G01N 33/53; G01N 33/537; G01N 33/543
[52] U.S. Cl. ..................... 435/7.2; 435/7.9; 435/7.92; 435/7.95; 435/805; 435/971; 435/973; 436/518; 436/523; 436/527; 436/530; 436/531; 436/538
[58] Field of Search ............... 435/7.2, 7.9, 7.92–7.95, 435/805, 968–971, 973; 422/55–60; 436/518, 523, 527, 530, 531, 538, 804, 810, 822

[56] References Cited

U.S. PATENT DOCUMENTS

| | | | |
|---|---|---|---|
| Re. 34,394 | 9/1993 | Bunting | 436/500 |
| 4,366,241 | 12/1982 | Tom et al. | 435/7.9 X |
| 4,434,236 | 2/1984 | Freytag | 436/512 |
| 4,803,170 | 2/1989 | Stanton et al. | 436/518 |
| 4,806,312 | 2/1989 | Greenquist | 422/58 X |
| 4,861,711 | 8/1989 | Friesen et al. | 435/970 X |
| 4,956,275 | 9/1990 | Zuk et al. | 436/518 X |
| 4,959,305 | 9/1990 | Woodrum | 435/805 X |
| 4,981,786 | 1/1991 | Dafforn et al. | 422/58 X |
| 4,999,285 | 3/1991 | Stiso | 435/7.9 |
| 5,008,080 | 4/1991 | Brown, III et al. | 422/56 |
| 5,028,535 | 7/1991 | Buechler et al. | 435/7.1 |
| 5,073,484 | 12/1991 | Swanson et al. | 435/7.92 |
| 5,075,078 | 12/1991 | Osikowicz et al. | 422/56 |
| 5,089,391 | 2/1992 | Buechler et al. | 435/7.1 |
| 5,114,673 | 5/1992 | Berger et al. | 422/56 |
| 5,143,852 | 9/1992 | Valkirs et al. | 436/501 |

FOREIGN PATENT DOCUMENTS

| | | | |
|---|---|---|---|
| 0362809 | 4/1990 | European Pat. Off. | 435/970 |
| 8905978 | 6/1989 | WIPO | 435/805 |
| WO91/12528 | 8/1991 | WIPO | 422/56 |

OTHER PUBLICATIONS

W. Dandliker et al, "Equilibrium and Kinetic Inhibition Assays . . . " in *Methods in Enzymology*, vol. 74 (1981) pp. 3–29.
S. Nerenberg et al, "Development and Clinical Applications of Radio-immunoassay . . . " in Methods in Enzymology vol. 73 (1981) pp. 666–691.
E. Maggio (ed) Enzyme-Immunoassay (CRC Press Inc. 1980) pp. 5–52.
B. Davis et al (ed) Microbiology-third edition (Harper & Row Inc. 1980) pp. 297–336.
W. Herbert et al (ed) A Dictionary of Immunology (Blackwell Scientific Publications 2nd ed. 1977.) p. 19.

*Primary Examiner*—Toni R. Scheiner
*Attorney, Agent, or Firm*—Klauber & Jackson

[57] ABSTRACT

An assay provides for detecting the presence of an analyte in a sample. Sample is applied to move through three zones. A mobilizeable receptor capable of binding to the analyte is present in the first zone. A trap for unbound receptor, consisting of immobilized ligand, is present in the second zone. Receptor bound to analyte will not bind to the ligand; unbound receptor will bind to the ligand. Mobilization and migration of the receptor can be detected in the third zone, which positively indicates that analyte is present. A device for carrying out the method is also provided.

11 Claims, 1 Drawing Sheet

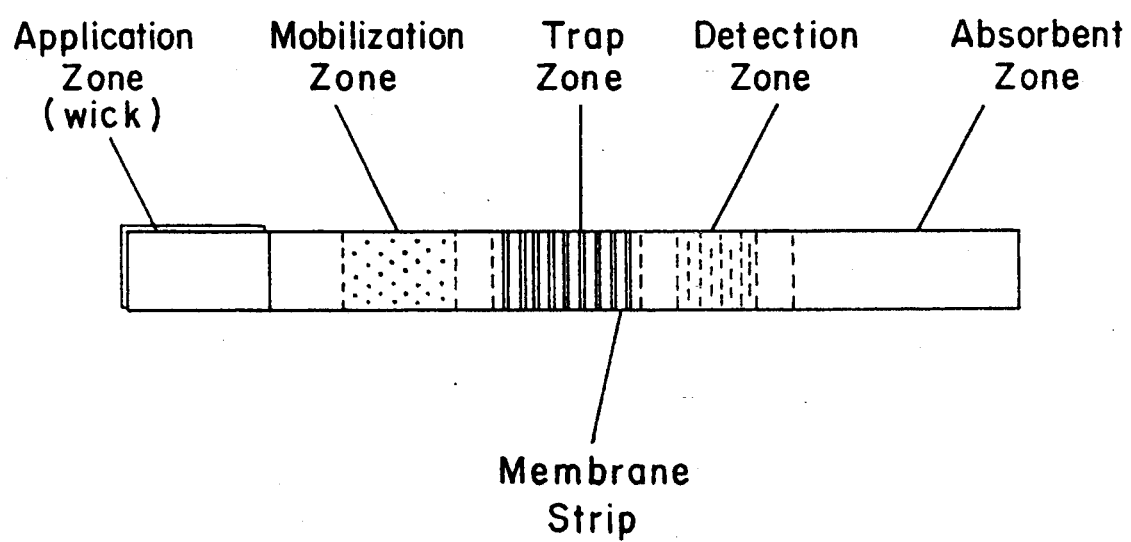

METHOD AND DEVICE FOR DETECTING THE PRESENCE OF ANALYTE IN A SAMPLE

FIELD OF THE INVENTION

The present invention relates to an assay method for detecting the presence of analyte in a sample and a device and kits for performing the same. The assay can be performed in a single apparatus for use in a laboratory or a field setting.

BACKGROUND OF THE INVENTION

Immunoassays utilize the specific binding capabilities of antibodies to detect the presence of target molecules in solution. Although the general principle is applicable to a broad range of problems, major commercial interest has centered on medical diagnostic applications for a wide variety of analytes in biological fluids such as blood, saliva, and urine.

Several types of immunoassays, useful for distinct applications, already exist. Each such assay type requires a way of distinguishing whether binding sites on an antibody are occupied or free. Typically this is accomplished by means of label such as an atom, molecule, enzyme or particle attached permanently to either the antibody or to an analog of the analyte.

There is a need for quick, accurate, simple assays that can be performed by laboratory personnel as well as by non-technical personnel outside of a laboratory setting. Such assays are necessary as society becomes increasingly concerned about the use of drugs, tobacco and alcohol. For example, in the workplace, testing for drug use is becoming more common. Insurance companies also need to establish whether a client uses tobacco or illicit drugs to calculate risk and establish insurability. Police officers in the field frequently administer tests for alcohol use; simple tests for use of illicit or impairing drugs would similarly aid law enforcement.

It is an object of the present invention to provide an assay method and a device for performing the assay that allows detection of an analyte in a sample under either laboratory or field conditions.

SUMMARY OF THE INVENTION

The assay method of the present invention provides for moving a sample suspected of containing an analyte through three zones, a first mobilization zone, a second trap zone, and a third detection zone, arranged so that the first mobilization zone and the third detection zone are spaced apart by the second trap zone. Receptor specific for the analyte of interest is provided on the first zone, the second zone has immobilized ligand and the third zone provides for detection of a receptor-analyte complex which positively correlates with the presence of analyte in the sample.

In practice, sample is applied to the first zone, and movement of sample through the first zone mobilizes receptor. If analyte is present in the sample, analyte and receptor will bind to form a stable receptor-analyte complex. The receptor-analyte complex moves through the second trap zone, substantially unaffected by the immobilized ligand, and into the third zone, where it is detected by a positive signal correlating with the presence of analyte in sample. If no analyte is present, mobilized receptor binds to the immobilized ligand in the trap zone so that no detection occurs in the detection zone, i.e., a negative result.

DEFINITIONS

Analyte—molecule of interest in an assay.

Ligand—molecule capable of binding to a receptor specific for analyte but not to receptor-analyte complex. The ligand is immobilized in the trap zone.

Receptor—molecule capable of specifically binding to either analyte or ligand, e.g., a cell surface receptor or an antibody. The receptor binds to analyte such that a stable receptor-analyte complex is formed which is substantially unaffected by the presence of immobilized ligand.

BRIEF DESCRIPTION OF THE DRAWINGS

FIG. 1 is a schematic view of the mobilization, trap and detection zones in a membrane strip.

DETAILED DESCRIPTION OF THE INVENTION

In accordance with the present invention a method for detecting the presence of an analyte in a sample and kits therefor are provided. A test sample can be any liquid suspected of containing the target analyte. Preferably the liquid comprises a body fluid, such as urine, blood, serum, plasma, saliva, bodily exudate, etc.

The assay method of the present invention provides for moving a sample suspected of containing an analyte through a pathway of three zones, a first mobilization zone, a second trap zone, and a third detection zone, arranged so that the first mobilization zone and the third detection zone are spaced apart by the second trap zone. Receptor specific for the analyte of interest is provided on the first zone, the second zone has immobilized ligand and the third zone provides for detection of a receptor-analyte complex which positively correlates with the presence of analyte in the sample.

In practice, sample is applied to the first zone. Movement of sample through the first zone mobilizes receptor. If analyte is present in the sample, analyte and receptor will bind to form a stable receptor-analyte complex. The receptor-analyte complex then moves through the trap zone, which contains immobilized ligand. The stability of the receptor-analyte complex is substantially unaffected by the immobilized ligand which migrates into the third detection zone. Detection of the receptor-analyte complex in the third zone positively correlates with the presence of analyte. If no analyte is present, mobilized receptor binds to the immobilized ligand in the trap zone so that no detection occurs in the detection zone, i.e., a negative result.

Suitable pathways for use in the invention provide means for movement of sample through the zones. For example, all three zones may be arranged on a single solid phase support which provides for movement of the sample through the zones, as by capillary action. Alternatively different materials may be used to construct each zone. The solid phase support may be a sheet or film with the zones arrayed sequentially along a sample pathway. A Nylon membrane is the preferred solid phase support for this purpose, although any solid phase which permits movement of the sample through the three zones may be used. Other suitable solid phase supports for use in the assay include, but are not limited to, coated plastic and coated glass, e.g., such as is used for thin layer chromatography, filters, polymer beads, silica gel, paper, membranes, agarose gel, polyacrylamide gel, gelatin, etc. Alternatively, a column packed with the support may be used. According to one embodiment of the invention, the first and third zone may be in liquid phase, with only the trap zone in solid phase. Any arrangement of zones on liquid or solid phase is contemplated as long as movement of sample through the zones is accomplished and the trap zone effectively binds mobilized receptor which is not bound to analyte.

It is contemplated that other means of moving sample through the zones of the invention, such as gravity, centrifugal force, and agitation, may be provided, and are within the scope of the invention.

The amount of sample required for an assay can be easily determined based on the particular arrangement of zones selected. For example, the amount of sample required when all three zones are arranged on a single solid phase support may differ from the amount required if only the trap zone is a solid phase. In a preferred embodiment, when the support is a nylon membrane 0.5×6 cm in size, 200 µl of sample are applied.

Nevertheless, if necessary, additional liquid may be added at any point along the pathway to maintain continuous migration of sample and to enhance readability of signal. Preferably the liquid will be a physiologically buffered solution, such as phosphate buffered saline, but other liquids or buffers may be chosen depending on the analyte of interest or means of detecting migration of receptor.

It will be clear that any arrangement that provides a series of three or more zones in communication so that liquid will move from the first zone through the second zone into the third zone may be used in the method of the invention. For example, in addition to a linear arrangement of discrete zones, the zones may also be arranged radially. In addition to the basic three zones already described, the sample pathway may also include an application zone for applying sample, and/or an absorbent zone which facilitates movement of the sample through the zones. See FIG. 1.

In a preferred embodiment, a control marker can be provided to indicate whether the liquid sample has moved through all the zones required for the assay, and to establish an end point for the assay. The control marker is mobilized by the sample fluid and moves to an end point located within or beyond the detection zone, where the presence of the control marker can be detected. The control marker can be disposed anywhere along the pathway where it will be mobilized by the sample liquid provided its detection can be distinguished from detection of either receptor-analyte complex or ligand. For instance, as exemplified herein, the control marker may be incorporated into the absorbent zone and its movement detected. In alternative embodiments, the control marker may be included in the mobilization zone and detected in the detection zone or absorbent zone. Control markers for use in the present invention comprise any detectable marker in the mobilization zone that can be mobilized by sample and will migrate into the detection zone or beyond as an indicator that the assay has operated properly. In a preferred embodiment, the control marker will comprise an inert protein, such as albumin or a molecule which mimics the size and composition of the mobilized receptor or ligand. For example, where the receptor is an antibody specific for analyte, the control marker may be a non-relevant antibody. In other embodiments, the control marker may be a dye, a latex particle or an enzyme.

The assay comprising receptor, ligand and means of detecting migration of receptor to the detection zone has particular utility for analyzing a sample for the presence of a small molecule such as a drug or drug metabolite. Detecting the presence of drugs or drug metabolites in a sample of body fluid from a subject is important for many applications. The presence of drugs or drug metabolites affects the choice of proper medical treatment, especially under emergency conditions. The medical industry also requires reliable data about smoking and drug use to assess the patient's condition. Detection of drugs or drug metabolites in a person is also important in law enforcement, the transportation industry, the military, in employment generally, in schools and athletics. Samples may be from any source, but preferably are from an animal, and more preferably from a human. Samples may be body fluid such as blood, plasma, serum, urine, saliva or bodily exudates.

Analytes may be any antigen, but small analytes (MW of 100 to 1000 Daltons) are of primary interest. Such analytes include therapeutic drugs and metabolites thereof, illicit drugs and metabolites thereof, steroids, and peptide hormones. Nevertheless, assays may be for larger molecules such as protein hormones, e.g., insulin, or viral antigens, bacterial antigens, serum proteins, antibodies or any antigen of interest where detection of the presence (or absence) of the analyte in a rapid, specific, sensitive assay is desirable.

Assays may be performed according to the present method in the field as well as the laboratory. Thus emergency medical personnel, police officers, medical technologists, and others will have ready access to sensitive, reproducible assays under field conditions, particularly when the label is visual and self indicating, i.e., does not require a secondary reaction or instrument for detection. An example of such a label is a colored latex particle, dye polymer or colloidal gold.

It also will be appreciated that the system can be reversed, i.e., that the first zone, the mobilization zone, may comprise ligand and the second zone, the trap zone, may comprise immobilized receptor. In this instance, introduction of sample onto the first zone mobilizes ligand which travels along with sample through the second zone containing immobilized receptor. If analyte is present in the sample it binds, i.e., is trapped by the immobilized receptor and free ligand moves into the detection zone. If no analyte is in the sample, ligand is trapped by the immobilized receptor and no detection occurs in the detection zone. Accordingly, the presence of analyte is indicated by movement of ligand to the detection zone.

THE MOBILIZATION ZONE

The mobilization zone of the invention preferably comprises a mobilizeable receptor capable of binding to the analyte. The receptor is mobilized by addition of liquid sample to the first zone. Receptor must be capable of moving with sample through the other zones without becoming non-specifically immobilized. As previously mentioned, alternatively, mobilizeable ligand may be present in the first zone.

In one preferred embodiment a control marker may be provided in addition to receptor. The control marker, like receptor is mobilized upon the introduction of liquid sample. Unlike receptor, control marker travels unhindered through all zones terminating in the detection zone or beyond where it generates a signal indicating that the assay system has worked properly.

When using a solid phase support, non-specific immobilization can be prevented by treatment of the support with a blocking agent, such as albumin or gelatin. Also, movement of the receptor through the zones should not be sterically hindered. A solid support selected for this purpose should therefore have pathways of a size which permit movement of the mobilizeable components of the system, e.g., receptor, receptor-analyte complex or ligand as the case may be.

The receptor has one or more binding sites capable of specifically binding to analyte and to ligand, but not both simultaneously. Preferably the receptor binds analyte with a high association constant and ligand with a low association constant. This will ensure that receptor bound to analyte form a stable receptor-analyte complex which will not bind to ligand.

Suitable receptors for use in assays of the invention include antibodies, cell surface receptors (or a fragment of a cell surface receptor that contains the binding site of analyte and ligand), enzymes (or the substrate binding site of an enzyme), or any other molecule or macromolecule capable of specifically binding to and forming a complex with a ligand and complex with an analyte. Antibodies and cell surface receptors are preferred, with antibodies more preferred. In a preferred embodiment, receptor is generated or selected to be specific for the most unique epitope on the analyte.

Various procedures known in the art may be used for the production of antibodies to analytes of interest. Such antibodies include but are not limited to polyclonal, monoclonal, chimeric, single chain, Fab fragments and an Fab expression library. For the production of antibodies, various host animals, including but not limited to rabbits, mice, rats, etc., may be immunized by injection with a particular analyte or analyte conjugated to an immunogenic carrier. Preferably analyte-carrier conjugates are prepared so that the most unique epitope of the analyte will be most accessible to antibody. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Monoclonal antibodies to analytes may be prepared by using any technique which provides for the production of antibody molecules by continuous cell lines in culture. These include but are not limited to the hybridoma technique originally described by Kohler and Milstein, (Nature, 1975, 256:495–497), the more recent human B-cell hybridoma technique (Kosbor et al., 1983, Immunology Today, 4:72) and the EBV-hybridoma technique (Cole et al., 1985, Monoclonal Antibodies and Cancer Therapy, Alan R. Liss, Inc., pp. 77–96). In an additional embodiment of the invention monoclonal antibodies specific to analytes may be produced in germ-free animals utilizing recent technology (PCT/US90/02545). According to the invention, human antibodies may be used and can be obtained by using human hybridomas (Cote at al., 1983, Proc. Natl. Acad. Sci., 80:2026-2030) or by transforming human B cells with EBV virus in vitro (Cole et al., 1985, in, Monoclonal Antibodies and Cancer Therapy, Alan R. Liss, pp. 77–96). In fact, according to the invention, techniques developed for the production of "chimeric antibodies" (Morrison et al., 1984, Proc. Natl. Acad. Sci., 81:6851-6855; Neuberger et al., 1984, Nature, 312:604-608; Takeda et al., 1985, Nature, 314:452-454) by splicing the genes from a mouse antibody molecule of appropriate antigen specificity together with genes from a human antibody molecule of appropriate biological activity can be used; such antibodies are within the scope of this invention.

According to the invention, techniques described for the production of single chain antibodies (U.S. Pat. No. 4,946,778) can be adapted to produce analyte-specific single chain antibodies. An additional embodiment of the invention utilizes the techniques described for the construction of Fab expression libraries (Huse et al., 1989, Science, 246:1275–1281) to allow rapid and easy identification of monoclonal Fab fragments with the desired specificity to analytes.

Antibody fragments which contain sites specific for analytes may be generated by known techniques. For example, such fragments include but are not limited to: the $F(ab')_2$ fragments which can be produced by pepsin digestion of the antibody molecule and the Fab fragments which can be generated by reducing the disulfide bridges of the $F(ab')_2$ fragments.

Alternatively, polyclonal or monoclonal antibody specific for an analyte of interest may be obtained from commercial sources.

Receptor for binding analyte may be purified, e.g., by affinity chromatography or low affinity chromatography. Monoclonal antibody may also be purified by protein A or anti-Immunoglobulin chromatography. Techniques for purifying polyclonal and monoclonal antibodies are well known in the art. In a preferred embodiment, a heterogenous receptor preparation, such as polyclonal antibody, may also be adsorbed with a low concentration (e.g., 1% of the receptor concentration) of ligand to remove any receptors capable of binding ligand with high affinity.

THE TRAP ZONE

The trap zone of the invention comprises immobilized ligand that will bind, i.e., trap, free receptor moving through the trap zone, but will not bind receptor bound in a receptor-analyte complex. Typically, the ligand is immobilized on a solid phase support. Alternatively, if the first zone contains mobilizeable ligand, the trap zone contains immobilized receptor. Solid phase supports for use in the invention are described in section 5, supra.

Immobilization on the solid phase support includes covalent, non-covalent or ionic associations or steric sieving. When ligand comprises protein, the solid phase support may be coated by adsorption of the protein to the solid phase. Alternatively, a crosslinking agent, such as glutaraldehyde, can be used to immobilize ligand. In another embodiment, as shown in the Example, infra, latex particles that are too large to move through the spaces of the solid phase support can be coated with ligand and the coated particles immobilized on the membrane. In a preferred embodiment, both ligand and latex particles are coated with ligand are immobilized on the solid phase support.

The ligand is capable of specifically binding to the receptor but not to receptor-analyte complex. Preferably the association constant of binding receptor to ligand is low as compared to that of analyte to receptor so that ligand does not affect the stability of a receptor-analyte complex. Thus, when receptor-analyte complex contacts ligand in the trap zone, the complex is not disrupted and moves into the detection zone. Conversely, when ligand contacts receptor-analyte complex in the trap zone, the stability of that complex is unaffected, and ligand moves into the detection zone.

Ligand may comprise an analog of the analyte, including an epitope of the analyte, a derivative of the analyte, a modified analyte, or an isomer of the analyte. Preferably the ligand differs from analyte at or near the receptor binding epitope. These differences may include steric, configurational, conformational or ionic changes. However, under certain circumstances analyte may function as ligand. For example, when ligand is immobilized in the trap zone, ligand may comprise analyte altered only by virtue of its linkage to a solid support in such a way as to reduce the analyte's affinity for receptor.

Analogs of analyte include the analogous molecule from a related species of animal, where such exists, or molecules prepared to structurally mimic the analyte. Such structural mimics may be, but need not be, chemically similar to the analyte, so long as the epitope is chemically similar. For example, a peptide may mimic the epitope of a protein, or even of a whole organism, and this serves as an analog of the protein. A suitable analog will simply share a receptor binding epitope or part of an epitope of the analyte.

Derivatives of analyte may be prepared by adding or deleting functional groups to the molecule. Derivatives may also be natural metabolic products of the analyte. One of ordinary skill will readily know how to prepare or identify derivatives of analytes for use in the invention. Preferably changes in molecular structure of the analyte will alter the receptor binding epitope composition or conformation in order to decrease the binding affinity of receptor for ligand.

Modified analyte includes analyte conjugated to a carrier protein. Addition of bulky groups, such as aromatic or cyclic molecules, to the analyte or to the protein can result in decreased binding affinity for receptor due to steric interference. Alternatively, conjugation with a bulky group may cause a conformational change in the receptor binding site of ligand that decreases binding affinity. Chemical modifications well known in the art may be used to modify ligand.

Isomers of analytes are molecules with the same composition but different configuration. Typically, isomers will have a different configuration at a particular carbon center, e.g., cis versus trans, D versus L. Isomers include diastereomers, which have the opposite configuration at one or more chiral centers, and include enantiomers of analytes. Since biological binding interactions depend on configuration as well as conformation and composition, use of an isomer as ligand can result in much lower binding affinity for receptor.

Where the analyte is a protein, the ligand may be prepared by recombinant DNA methods using site directed or other mutagenesis techniques to alter the amino acid sequence of the protein. These techniques are well known to those skilled in the art (e.g., see Zoller and Smith, 1984, DNA 3:479–488; Oliphant et al., 1986, Gene 44:177; Hutchinson et al., 1986, Proc. Nat'l. Acad. Sci. U.S.A. 83:710). Polymerase chain reaction (PCR) techniques are preferred for site directed mmutagenesis (see Higuchi, 1989, "Using PCR to Engineer DNA," in PCR Technology: Principles and Applications for DNA Amplification, H. Erlich, ed. Stockton Press, Chapter 6, pp. 61–70).

The ligand may further comprise a carrier protein. The carrier protein may be an essentially inert protein such as albumin or keyhole limpet hemocyanin, but a carrier protein should not be the same carrier used, if any, for immunization to produce antibody to the analyte. An enzyme label may be a carrier protein.

Ligand may also comprise a linking group. A linking group may space ligand from carrier protein. An example of a spacer linking group is ε-aminocaproic acid. Also, bulky linking groups may be used to sterically hinder binding of receptor to ligand and thus decrease the binding affinity of receptor and ligand. An example of bulky linking group is p-aminobenzoic acid.

THE DETECTION ZONE

The present invention provides means for positively detecting receptor-analyte complex in the detection zone. Alternatively, if ligand is mobilized upon introduction of the sample and receptor is immobilized in the trap zone, then free ligand migrates into the detection zone when analyte is present in the sample and provides a positive signal. Positive detection means that signal positively correlates with the presence of analyte in a sample. A positive correlation is advantageous because it is psychologically satisfying that the presence of signal or increase in signal intensity indicates presence of analyte in a sample. Both sophisticated diagnostic laboratories and non-technical personnel benefit from the use of an assay in which a signal means only a positive result because such results are not susceptible to misinterpretation, as may occur when the absence of signal indicates presence of analyte.

In a preferred embodiment, detecting the receptor-analyte complex in the detection zone is by means of observing a signal from a label attached to the receptor. Suitable labels include enzymes, fluorophores, chromophores, radioisotopes, dyes, colloidal gold, latex particles, and chemiluminescent agents. When a control marker is employed, the same or different labels may be used for the receptor and control marker.

In a preferred embodiment, a label may be a colored latex particle. When labeled receptor-analyte complex and/or control marker moves into the detection zone, a colored band or spot will appear.

Label may also be an enzyme. In one instance when the label is an enzyme, the detection zone may comprise substrate for an insoluble chromogenic product. When enzyme conjugated to receptor-analyte complex moves into the detection zone, the enzyme catalyzes formation of colored product. Alternatively, substrate for the enzyme label may be added after migration is complete.

Other labels suitable for use will be apparent to those of ordinary skill. For example, fluorescent labels may be seen under ultraviolet irradiation. Chemiluminescent labels may be seen by addition of reagents to stimulate luminescences, such as a reductant or an oxidant. Choice of detection means can be made on the basis of convenience for the practitioner. Various detection means known in the art fall within the scope of the present invention.

Preferably the detection zone comprises an immobilized binding partner of the receptor. The binding partner binds receptor bound to the analyte. Upon migration to the detection zone, the receptor-analyte complex is bound and immobilized by the binding partner. In an alternative embodiment, binding partner binds free ligand which migrates into the detection zone.

The specific binding partner of receptor may be antibody. When receptor is antibody, the binding partner may be specific for antibody isotype, allotype, or xenotype. Use of more than one antibody as receptor, each specific for a unique analyte and each of a different isotype, allotype or xenotype, allows use of isotype, allotype or xenotype specific binding partners in multiple sections of the detection zone.

Other suitable binding partners for use in the detection zone will be readily apparent from this disclosure. For example, receptor may be conjugated with a protein or epitope, and the detection zone may comprise a binding partner specific for the protein or epitope. In another embodiment, latex beads may carry additional protein or epitope that allow the bead to be recognized by a binding partner in the detection zone. More than one protein or epitope can be used in combination with more than one immobilized binding partner to detect more than one analyte.

PREFERRED EMBODIMENTS

In addition to the three zones already discussed, in preferred embodiments further zones may be provided. These include an application zone useful for applying sample and an absorbent zone which is useful for facilitating migration of the sample through the other zones. Also, a control marker may be included which provides a signal indicating proper operation of the assay.

Thus, in one preferred embodiment, sample is applied to an application zone and then migrates to the mobilization zone. The application zone may be a reservoir, filter, or wick, although any form of application zone is suitable as long as it uniformly delivers the sample to the mobilization zone. The application zone may also be designed to function as a filter for removing undesirable particles from a sample.

An absorbent zone is used to enhance liquid migration through the zones. The absorbent zone, may be an extension of the solid phase support, a hydrogel or filter paper, or any other material which facilitates migration of liquid through the zones on the solid phase support, e.g., by increasing capillary action. The absorbent zone may include an indicator to show entry of sufficient fluid into the system such as, a Ph indicator, a dye, or an adulterant indicator. In a preferred embodiment, the absorbent zone is simply an extension of the solid phase support. Such indicators may be used to confirm that assay conditions are within allowable parameters.

In another preferred embodiment, a control marker is mobilized by sample and detected in the detection zone or beyond. Detection of the control marker depends on migration of sample, and is not affected by the presence or absence of analyte in the sample. The control marker may be detected in the detection zone or in the absorbent zone, if present. A binding partner of the marker can be used to immobilize the marker in the third zone for detection.

Detection of a control marker must be distinguishable from detection of receptor-analyte complex, or free ligand. This may be accomplished by providing discrete regions within the detection zone for detecting receptor-analyte complex and control marker, or by using different labels for each. When the labels are colored latex particles, a different colored latex may be used for the receptor-analyte complex and for the control marker. Alternatively the visual appearance of the assay signal, such as shape, may be clearly different for the control and for detection of the analyte.

In one embodiment, binding partners of the receptor-analyte complex and the control marker can be immobilized in the detection zone at right angles in the shape of a plus ("+") sign. Binding of control marker only will appear as a "−" sign; binding of control marker and analyte will appear as a "+" sign. An advantage of a latex particle is that the label signal, i.e., color, is stable over a long period of time. Thus, the positive or negative result of an assay can be directly observed as well as recorded. Availability of the result of an assay in a permanent form, rather than reliance solely on an observer's interpretation of the result, affords a further opportunity to confirm assay results.

An alternate embodiment is provided by the working examples infra. In yet another preferred embodiment, the invention provides a method to detect the presence of more than one analyte in a sample. In this embodiment, each zone, the mobilization zone, trap zone and detection zone contains more than one receptor, immobilized ligand and detector, respectively. The detection zone comprises more than one immobilized binding partner of more than one receptor-analyte complex arranged in discrete sections of the detection zone. Each binding partner is specific for a unique receptor-analyte complex, each receptor being specific for a unique analyte. Such an arrangement provides for detection of more than one analyte in a single sample. In another embodiment for simultaneously assaying multiple analytes, different receptors may be labeled differently, e.g., with different colored latex beads or different fluorophores. Detection of more than one analyte in a sample reduces the amount of time and sample that would be needed for multiple assays, provides for analysis of a standard sample size for multiple analytes, and minimizes inconvenience to the person being tested and to the practitioner.

THE DEVICE

In one embodiment of the invention, a device is provided to perform the assay method. The device comprises three zones as described supra. In a preferred embodiment, the device further comprises a housing dimensioned to substantially fit the zones. The housing can provide structural support for the zones. Materials for use in the housing include, but are not limited to, transparent tape, plastic film, plastic, glass, metal and wood, with tape, plastic film and plastic preferred. The housing has an opening to apply sample, preferably to an application zone, and a window or opening in the detection zone to observe results.

Where more than one analyte may be detected, markings may be present on the housing to indicate the presence of which analyte is detected. The housing may also mark to indicate where to apply sample may also be included.

Preferably the zones are on a solid phase support; more preferably, the solid phase support is a nylon membrane, but other solid phase supports described herein or known to those skilled in the art are suitable.

In a preferred embodiment, the means for detection will comprise colored latex beads.

As will be readily appreciated, the present device will provide numerous advantages. The person who administers the assay need not come in contact with sample. The entire assay is performed by application of sample to the device. Application of sample is easy. A large number of devices can be provided for use at any time.

The invention will be further clarified by the following Examples, which are intended to be purely exemplary of the invention and not as limitations of the invention. Indeed, various modifications of the invention in addition to those shown and described herein will become apparent to those skilled in the art from the description and accompanying drawings. Such modifications are intended to fall within the scope of the appended claims.

EXAMPLE: DETECTION OF BENZOYLECGONINE IN A SAMPLE

The present example demonstrates the use of a device for detecting the presence of a small molecule metabolite of cocaine, benzoylecgonine, in a sample. The device consists of a membrane along which sample passes from an application zone through mobilization, trap and detection zones to an absorbent zone. Appearance of a color in the detection zone indicates benzoylecgonine is present.

In this example the mobilization zone contains receptor and the trap zone has immobilized ligand, and a control marker is provided. The control marker and its binding partner were spaced apart in the absorbent zone, so that movement of the sample fluid through the absorbent zone was detected. In particular, detection of the control marker bound to its immobilized binding partner indicated that the sample fluid moved through each zone of the device and that the assay operated properly. This arrangement of the assay system allowed for a positive signal which indicated completion of the assay. One hundred five human urine samples were tested by the method of the invention and by a standard ELISA technique. The results obtained using the assay method of the present invention correlated well with the results obtained by ELISA.

MATERIALS AND METHOD

PREPARATION OF RECEPTOR, LIGAND AND BINDING PARTNER

Receptor. Blue dyed latex particles (0.318$\mu$ diameter, Seradyn, IN) were coated with a solution of mouse monoclonal anti-benzoylecgonine IgG overnight at room temperature in 0.05M phosphate buffer, pH 7.2–7.5. The final concentration of blue latex was 0.25% and of monoclonal antibody was 150 $\mu$g/ml. The particles were washed twice with 5 mg/ml BSA in phosphate buffer, pH 7.2–7.5, and the conjugate suspended at 5% latex in phosphate buffer containing 5 mg/ml BSA.

Ligand. Bovine gamma globulin (30 mg) was chemically coupled to ecgonine (26 mg) directly, or through an appropriate linker, using the NHS (N-hydroxysuccinimide) and carbodiimide method. The complex was dialyzed against PBS and stored at 4° C. at a concentration of 2.5 mg/ml bovine gamma globulin in PBS. The covalently linked bovine gamma globulin-ecgonine complex was coated on white latex (1–3$\mu$ diameter, Seradyn IN) by overnight incubation at room temperature in 0.05M phosphate buffer. A concentration of 150 $\mu$g/ml of bovine gamma globulin was used, with the white latex at 0.25%. The ligand coated latex particles were washed twice with 5 mg/ml BSA in pH 7.2–7.5 phosphate buffer, and suspended at 5% latex in phosphate buffer containing 5 mg/ml BSA.

Binding partner. White latex particles (1–3$\mu$ diameter, Seradyn, IN) were coated with a solution of goat anti-mouse IgG overnight at room temperature in 0.05M phosphate buffer, pH 7.2–7.5. The final concentration of white latex was 0.25% and of goat anti-mouse IgG was 150 $\mu$g/ml. The particles were washed twice with 5 mg/ml BSA in phosphate buffer, pH 7.2–7.5, and the conjugate suspended at 5% in phosphate buffer containing 5 mg/ml BSA.

Control Marker: Blue dyed latex particles (0.318$\mu$ diameter, Seradyn, IN) were coated with a solution of mouse IgG overnight at room temperature in 0.05M. Phosphate buffer, pH 7.2–7.5. The final concentration of blue latex was 0.25% and of mouse IgG 100 $\mu$g/ml. The particles were washed twice with 5 mg/ml BSA in phosphate buffer, pH 7.2–7.5, and the conjugate suspended at 0.5% in phosphate buffer containing 5 mg/ml BSA.

PREPARATION OF THE ASSAY

The application zone consisted of wicking paper, (Schleicher & Schuell, 300, 470 or 900, Keene, NH), that was cut into small pads approximately 5/32"×½". Nylon membranes (5 $\mu$m pore size; Biodyne A available from Pall Biomembranes, Glen Cove, N.Y.), were cut into 5×10 cm portions and soaked at room temperature for 30 minutes with agitation in an aqueous solution of 0.5% casein, 5% sucrose, 0.05% TRITON X-100, 0.05M Tris, 0.002M $MgCl_2$, 0.9% NaCl, 0.2% $NaN_3$, pH 8.0. The membranes were allowed to air dry at room temperature.

Ligand and binding partners for both receptor and control marker were applied to the membrane sheets in zones as described using a mechanized air-brush applicator with 25–75 psi nitrogen. Ligand and binding partner for receptor and control were applied at the rate of 2.5 $\mu$l/cm. The ligand was diluted in 0.5M $Na_2CO_3$ pH 9.3 buffer to 3000 $\mu$g/ml and the binding partner diluted to 500 $\mu$g/ml in the same buffer. The membrane sheets were allowed to air dry for 1 hr. at room temperature then were incubated at 37° C. for 30 min. The sheets were then soaked with agitation in an aqueous solution of 0.5% casein, 5% sucrose, 0.1% TRITON X-100, 0.05M Tris, 0.002M $MgCl_2$, 0.9% NaCl, 0.02% $NaN_3$ pH 8.0. The membrane sheets were allowed to air dry at room temperature for at least 4 hr.

Receptor, control marker and ligand-coated latex particles were applied to the membrane sheets in zones as shown in FIG. 1 using a mechanized air-brush applicator with 25–75 psi nitrogen. The receptor was diluted to 0.25% latex in 20% sucrose and one zone was applied at the rate of 2.5 $\mu$l/cm. Ligand-coated latex particles were diluted to 1% latex in 0.5M NaCO pH 9.3 buffer and two zones were applied at the rate of 25 $\mu$l/cm. Control marker was diluted to 0.15% latex in 20% sucrose and one zone was applied at the rate of 2.5 $\mu$l/cm. The coated membrane sheets were allowed to air dry at room temperature.

The membrane sheets were cut into strips, approximately 0.5×6 cm with each strip having receptor mobilization, trap detection and absorbent zones as shown in FIG. 1. In this example the absorbent zone served two purposes. As an extension of the nylon membrane past the detection zone, it enhanced capillary action facilitating movement of the sample through the device. Additionally, the absorbent zone contained the control marker followed by its binding partner, which served to indicate the end point of the assay and that it functioned properly. The mobilization zone included receptor (anti-benzoylecgonine antibody) coated on blue latex beads. The blue latex beads of 0.318$\mu$ diameter were chosen to be capable of migration through the nylon membrane. The trap zone included ligand (ecgonine conjugated to BGG) directly coated to the membrane, and on large (1–3$\mu$ diameter) latex beads that cannot migrate, thus providing a large, efficient trap zone. In the detection zone, binding partner of the receptor (goat-anti-mouse IgG) was adsorbed. The absorbent zone contained the control marker (normal murine IgG) coated on blue latex beads, followed by its immobilized binding partner (goat-anti-mouse IgG).

ASSAY FOR BENZOYLECGONINE

A membrane strip, an absorbent pad and an application wick were assembled in a suitable jig-type device so that there was continuous contact between the application wick and membrane, and the membrane and the absorbent pad (FIG. 1). The orientation of the individual parts was such that the application wick was at the receptor mobilization zone end of the membrane, and the absorbent pad was at the detection zone end. The sample, 200 μl of aqueous solution, was applied to the application wick and allowed to wick up the membrane through the receptor mobilization zone, trap and detection zone, to the absorbent pad.

RESULTS

Detection of benzoylecgonine in 105 human urine samples was compared to detection in the samples with a standard ELISA for benzoylecgonine. Assays were performed for one hour and for 10 minutes. The results of the assays are shown in Table 1.

TABLE 1

Comparison of Solid Phase Assay Device With ELISA to Detect Benzoylecgonine.

| | Analyte Detection by ELISA | |
|---|---|---|
| | + | − |
| Analyte Detection by the present method | | |
| + | 72 | 0 |
| − | 1 | 32 |

Accuracy = 104/105 = 99%
Sensitivity = 72/73 = 99%
Specificity = 32/32 = 100%

DISCUSSION

The results in Table 1 clearly show that the simple, easy to use method of the invention is comparable to ELISA for detecting the presence of a small molecule in a sample. In particular, 72 out of the 73 positives detected by ELISA were also positive using the assay of the invention. Likewise, 32 negatives detected by ELISA were also negative in the assay of the invention.

What is claimed is:

1. A method for detecting at least one analyte in a liquid sample comprising:
   (a) moving the sample along a pathway comprising three zones located on a single solid phase support, wherein the sample moves from a first zone comprising mobilizeable labeled receptor, which are mobilized by and move with the sample, which receptors specifically bind to and form labeled receptor-analyte complexes with analyte in the presence of analyte in the sample, to a second zone comprising immobilized ligand which binds the mobilized labeled receptors that are not complexed to analye and has a lower association constant than the analyte for the labeled receptor so that the immobilized ligand does not affect the stability of any labeled receptor-analyte complex formed by the moving sample and the labeled receptor and into a third zone for detecting the presence of the labeled receptor-analyte complex; and
   (b) detecting the presence of labeled receptor-analyte complexes in the third zone, which positively indicates the presence of analyte in the sample.

2. A method for detecting at least one analyte in a liquid sample comprising:
   (a) moving the sample along a pathway comprising three zones located on a single solid phase support, wherein the sample moves from a first zone comprising mobilizeable labeled ligands which are mobilized by and move with the sample, and have a lower association constant than the analyte for a receptor so that the labeled ligands do not affect the stability of any receptor-analyte complexes formed by the moving sample and receptors, to a second zone comprising receptors immobilized therein, which in the absence of analyte bind to mobilized labeled ligands, but in the presence of analyte bind to the analyte so that mobilized labeled ligands do not bind to the receptors and move into a third zone for detecting the presence of labeled ligands; and
   (b) detecting the presence of labeled ligands in the third zone, which positively indicates the presence of analyte in the sample.

3. The method of claim 1 or 2 in which the solid phase support is selected from the group consisting of coated plastic, coated glass, polymer beads, a filter, a silica gel, paper and a membrane.

4. The method of claim 1 or 2 in which the receptor is selected from the group consisting of an antibody having one or more binding sites for the analyte and the ligand, a fragment of an antibody having one or more binding sites for the analyte and the ligand, a cell surface receptor having one or more binding sites for the analyte and the ligand, and a fragment of a cell surface receptor having one or more binding sites for the analyte and the ligand.

5. The method of claim 1 or 2 in which the ligand is selected from the group consisting of analyte analogue, derivative, modification and isomer.

6. The method of claim 1 in which the third zone comprises an immobilized binding partner of the receptor.

7. The method of claim 2 in which the third zone comprises an immobilized binding partner of the labeled ligand.

8. The method of claim 1 or 2 in which the label is selected from the group consisting of an enzyme, a fluorophore, a chromophore, a dye, colloidal gold, a detectable latex particle and a chemiluminescent agent.

9. The method of claim 1 for detecting more than one analyte in the sample in which the first zone comprises more than one receptor, in which a receptor specific for each analyte is present, the second zone comprises more than one ligand, in which a ligand is present for each analyte is present, the second zone comprises more than one receptor, which a receptor is present for each analyte, and the detection zone comprises one binding partner specific for each receptor, wherein each binding partner is on a discrete area of the detection zone.

10. The method of claim 2 for detecting more than one analyte in the sample in which the first zone comprises more than one ligand, in which a ligand for each analyte is present, the second zone comprises more than one receptor, in which a receptor is present for each analyte, and the detection zone comprises one binding partner specific for each ligand, wherein each binding partner is on a discrete area of the detection zone.

11. The method of claim 1 or 2 in which the movement of the sample is facilitated by an absorbent zone which comprises an extension of a solid phase support or a hydrogel.

* * * * *